(12) United States Patent
Kim et al.

(10) Patent No.: US 7,927,829 B2
(45) Date of Patent: Apr. 19, 2011

(54) **METHOD FOR IN VITRO PHOSPHORYLATION OF TRAP OF *STAPHYLOCOCCUS AUREUS* AND A METHOD FOR SCREENING THE INHIBITOR OF THE TRAP PHOSPHORYLATION**

(75) Inventors: Kyeong Kyu Kim, Gyeonggi-do (KR); Sung Wook Kang, Gyeonggi-do (KR)

(73) Assignee: Sungkyunkwan University Foundation for Corporate Collaboration, Suwon-si, Gyeonggi-do (KR)

( * ) Notice: Subject to any disclaimer, the term of this patent is extended or adjusted under 35 U.S.C. 154(b) by 199 days.

(21) Appl. No.: 12/185,843

(22) Filed: Aug. 5, 2008

(65) Prior Publication Data

US 2009/0075308 A1    Mar. 19, 2009

(30) Foreign Application Priority Data

Aug. 7, 2007  (KR) .......................... 10-2007-0078982

(51) Int. Cl.
*C12Q 1/50* (2006.01)
(52) U.S. Cl. ........................................................ 435/17
(58) Field of Classification Search .................. None
See application file for complete search history.

(56) References Cited

OTHER PUBLICATIONS

Balaban et al. "Regulation of *Staphylococcus aureus* pathogenesis via target of RNAIII-activating protein (TRAP)", JBC, 2001, 276(4):2658-2667.*

* cited by examiner

*Primary Examiner* — Karen Cochrane Carlson
*Assistant Examiner* — Bin Shen
(74) *Attorney, Agent, or Firm* — The Nath Law Group; Joshua B. Goldberg; Mihsuhn Koh

(57) ABSTRACT

The present invention relates to a method for in vitro phosphorylation of TRAP derived from *Staphylococcus aureus*. In the present invention, the TRAP is first identified as a kinase that self-phosphorylates and is phosphorylated specifically in the presence of an oxidative metal ion such as iron, copper and zinc. Based upon this finding, a novel method for in vitro phosphorylation of purified TRAP is provided and also, a method for screening various chemicals and natural materials by using the above method is provided in order to select inhibitors against the TRAP phosphorylation. The inhibitors are expected to be applied for novel antibiotics of *Staphylococcus aureus*, because this TRAP phosphorylation is essential to infect *Staphylococcus aureus*. Therefore, the present invention can be widely used to develop novel drugs against *Staphylococcus aureus* and their resistant strains, in near future.

9 Claims, 7 Drawing Sheets

SEQUENCE LISTING

```
<160> NUMBER OF SEQ ID NOS: 1

<210> SEQ ID NO 1
<211> LENGTH: 504
<212> TYPE: DNA
<213> ORGANISM: Staphylococcus aureus

<400> SEQUENCE: 1
atgaagaaat tatatacatc ttatggcaca tatggatttt taaatcagat aaaaatcaat      60
aatccatctc atcatttatt ccaattttca actgctgatt catcggtgat ttttgaagag     120
actgaagaaa atactgtact gaaatcacct tcaatatatg aagttattaa agaaataggc     180
gcattcaatg aagatcattt ttattgcgca atttttattc cgtcaactga agaccatgtt     240
tatcaacttg aaaagaaatt aatcagtgtt gatgacaatt tcaaaaactt tggtggcttt     300
aaaagttatc gattgctaag acctgttaaa ggtacaacat acaaaattta ctttggcttt     360
gctgatcgac aaacttatga agactttaaa aattctgatg cttttaaaga tcatttttca     420
aaagaagcat taagtcatta ctttggttca agtggacaac attcaagtta ttttgaaaga     480
tatttatacc caataaaaga atag                                            504
```

METHOD FOR IN VITRO PHOSPHORYLATION OF TRAP OF *STAPHYLOCOCCUS AUREUS* AND A METHOD FOR SCREENING THE INHIBITOR OF THE TRAP PHOSPHORYLATION

CROSS-REFERENCE TO RELATED PATENT APPLICATION

This application claims the benefit of Korean Patent Application No. 10-2007-0078982, filed on Aug. 7, 2007, in the Korean Intellectual Property Office, the disclosure of which is incorporated herein in its entirety by reference.

REFERENCE FOR SEQUENCE LISTING SUBMITTED ELECTRONICALLY

The official copy of the sequence listing is submitted electronically via EFS-Web as an ASCII formatted sequence listing with a file name "30342U_Sequence_Listing.txt", created on Oct. 27, 2010 and having a size of 2 kilobytes. The sequence listing contained in this ASCII formatted document is part of the specification and is herein incorporated by reference in its entirety.

BACKGROUND OF THE INVENTION

1. Field of the Invention

The present invention relates to a method for in vitro phosphorylation of TRAP (target of RNA III-activating protein) derived from *Staphylococcus aureus* and a method for screening inhibitors against the TRAP phosphorylation.

2. Description of the Related Art

*Staphylococcus aureus* is a Gram-positive bacterium causing food poisonings and inflammatory diseases such as skin suppuration, tympanitis and cystitis, frequently found in the nature. *Staphylococcus aureus* also provokes various diseases in humans and animals, because it expresses and secretes hemolytic toxins, endotoxins, exotoxins, proteases, and the like [Lowy F. D., *Staphylococcus aureus* infections. 1998 *N. Engl. J. Med.*, 339:520-532]. In prior arts, it is reported that the toxin expression of *Staphylococcus aureus* is regulated by a transcriptional expression of RNA III. Also, the transcriptional expression of RNA III is elucidated to be regulated by a quorum sensing mechanism. In turn, the quorum sensing mechanism of *Staphylococcus aureus* is controlled by transcription-regulating proteins such as AIP (autoinducing peptide) and Rap (RNAIII activating protein) [Balaban N. et al., Autoinducer of virulence as a target for vaccine and therapy against *Staphylococcus aureus*. 1998 *Science*, 280:438-440; Novick R. P., Autoinduction and signal transduction in the regulation of staphylococcal virulence. (2003 *Mol. Microbiol.*, 48:1429-49). In detail, staphylococcal bacteria secrete the RAP protein, when reaching a certain density at a specified stage. The resulting RAP protein binds onto another staphylococcal bacterium so as to transmit a quorum sensing signal. The TRAP protein is involved in the signal transduction of quorum sensing by the RAP protein. It is reported that the phosphorylation of the TRAP protein at the 66th histidine residue is essential prior to the signal transduction [Gov Y., Quorum sensing in Staphylococci is regulated via phosphorylation of three conserved histidine residues. [2004 *J. Biol. Chem.*, 279:14665-72]. However, it is unknown yet how the TRAP phosphorylation is induced by the signal transduction of the RAP protein.

In addition, the signal transduction pathway for the quorum sensing is clarified to play a very important role during a staphylococcal infection. Actually, the expression of staphylococcal toxins and the biofilm formation are obstructed completely when the signal transduction is inhibited (Balaban N. et al., Regulation of *Staphylococcus aureus* pathogenesis via target of RNAIII-activating protein [200. *J. Biol. Chem.*, 276: 2658-2667]). Recently, it is reported that the Rap, an initial protein of the quorum sensing signal reduces the staphylococcal infection of mice remarkably, when being treated with a specific antibody against the RAP protein or blocked with a RNAIII inhibiting peptide (RIP), a RAP mediated quorum sensing inhibitor [Balaban N. et al., Treatment of *Staphylococcus aureus* biofilm infection by quorum sensing inhibitor RIP. 2007 *Antimicrobe Agents Chemother.*, 51:2226-2229]. It is also disclosed that the production of staphylococcal toxins decreases greatly and the bacterial infection decreases, when staphylococcal bacteria are mutated unable to express the TRAP or when its amino acid resides are substituted at a certain site so as not to be phosphorylated [Gov Y., Quorum sensing in Staphylococci is regulated via phosphorylation of three conserved histidine residues. 2004 *J. Biol. Chem.*, 279: 14665-72]. As a consequence, the Rap and the TRAP proteins of *Staphylococcus* are very important in initiating the host infection via the signal transduction. Especially, the TRAP phosphorylation is essential in determining the staphylococcal infection. Therefore, it is expected that inhibitors against the TRAP phosphorylation can be developed into a novel antibiotic to prevent the infection of *Staphylococcus* and other bacteria having similar proteins to the TRAP.

In order to identify the importance of the TRAP phosphorylation, Balaban et al. have phosphorylated the TRAP after culturing staphylococcal bacteria [Balaban N. et al., Regulation of *Staphylococcus aureus* pathogenesis via target of RNA III-activating protein. 2001, *J. Biol. Chem.*, 276:2658-2667; Gov Y. Quorum sensing in Staphylococci is regulated via phosphorylation of three conserved histidine residues. 2004, *J. Biol. Chem.*, 279:14665-72]. This technique is illustrated in U.S. Pat. No. 6,747,129. In the patent, the amino acids sequence of the TRAP and the method for TRAP phosphorylation using cultured staphylococcal bacteria by sending a quorum sensing signal via RAP protein are disclosed. In addition, Balaban et al. have reported in U.S. Pat. No. 6,291, 431 that the RIP peptide can block the staphylococcal infection effectively, when it is used to inhibit the TRAP phosphorylation. This result is illustrated in a recently published paper [Cirioni et al., RNAIII-inhibiting peptide significantly reduces bacterial load and enhances the effect of antibiotics in the treatment of central venous catheter-associated *Staphylococcus aureus* infections. 2006, *J. Infect. Dis.*, 193(2): 180-186]. Besides, Balaban et al. have confirmed that the RIP peptide can efficiently improve a germicidal activity, when being administered with an antibiotic, because it increases the drug sensitivity of staphylococcal bacteria [Balaban et al., RNAIII-inhibiting peptide inhibits in vivo biofilm formation by drug resistance *Staphylococcus aureus*. 2003, *Antimicrob. Agents Chemother.*, 47(6): 1979-1983; Balaban et. al, Treatment of *Staphylococcus aureus* biofilm infection by the quorum sensing inhibitor RIP. 2007, *Antimicrob. Agents Chemother.*, 51(6): 2226-2229]. As a consequence, it is clarified that the TRAP should be an effective target protein of staphylococcal bacteria in order to develop new antibiotics.

The TRAP is known to be phosphorylated within cells, when a quorum sensing signal is transmitted via the RAP protein. But the mechanism of TRAP phosphorylation has not been fully disclosed yet in patent documents or published papers. It is just conjectured that the Rap signal may be transferred from outside of a cell to inside through an unknown membrane protein and then, accepted by a certain protein kinase so as to phosphorylate the TRAP.

Presently, in order to measure the TRAP phosphorylation, microbes are cultured with media containing radioactive isotope-labelled phosphates. Then, a small amount of the TRAP protein is monitored in order to examine whether it binds with radioactive phosphates. This procedure is disadvantageous because it requires a lot of time and cost. Therefore, it seems that a method for in vitro phosphorylating the TRAP is more effective and convenient than the above method using radio-isotopes, in order to select inhibitors against the TRAP. Unfortunately, such a technique of in vitro phosphorylation has not disclosed yet, because the TRAP protein is not similar to any other known proteins in respect of the structure and function.

SUMMARY OF THE INVENTION

Therefore, the present invention has been made in view of the above problems. The present inventors have elucidated that the TRAP is a kinase phosphorylating itself even in the absence of a RAP protein and utilizes specifically oxidative metal ions such as iron, copper and zinc. Based upon this finding, we have developed a novel method for phosphorylating purified TRAPs in vitro. We have also attempted to provide a method for screening inhibitors against the TRAP phosphorylation based upon this technique, and completed this invention successfully.

It is an object of the present invention to provide a method for in vitro phosphorylation of TRAP (target of RNA III-activating protein).

It is another object of the present invention to provide a method for screening an inhibitor of the TRAP phosphorylation by using the above-mentioned method for in vitro phosphorylation. This method can be used to select inhibitors having an antibiotic efficacy upon staphylococcal bacteria.

In accordance with an aspect of the present invention, the above and other objects can be accomplished by the provision of a method for in vitro phosphorylation of TRAP derived from *Staphylococcus aureus* and, by using the above-mentioned method, a method for screening a phosphorylation inhibitor of the TRAP (target of RNA III-activating protein) that has an antibiotic efficacy upon staphylococcal bacteria.

In accordance with another aspect of the present invention, there is provided a method for in vitro phosphorylation of TRAP, which comprises a step: in vitro mixing a phosphorylation buffer, oxidizing ions of a transition metal and ATP with TRAP purified from cells.

In conventional methods, the TRAP is just known to be phosphorylated within cells, when a quorum sensing signal is transferred via RAP protein from outside of cells. Thus, the protein has been phosphorylated only in vivo by using a RAP protein. The present inventors have elucidated for the first time that the TRAP is a self-phosphorylating kinase. Based upon this finding, we have developed a method for in vitro phosphorylation of the TRAP without the RAP protein.

In another embodiment of the present invention, the TRAP is separated and purified from a bacterial transformant transformed with a TRAP expression vector after being expressed in a large scale. In detail, the expression vector Kim001 that can induce a production of exogenous proteins by using IPTG and express the TRAP protein having 6-histidine residues at the C-terminus is constructed as described in Example 1 (See FIG. 1). The expression vector Kim001 is transformed into *Escherichia coli* in order to produce the TRAP protein in a large scale and then, the TRAP protein is separated in high purity.

In another embodiment of the present invention, there is provided an additional step: measuring a degree of phosphorylation of the TRAP right after the above mixing step. In order to identify the degree of the TRAP phosphorylation, any method for measuring a kinase activity disclosed in prior arts can be used. Preferably, it can be selected from in vitro kinase assay using a luciferase (See Example 7) or SDS-PAGE using $P^{32}$-ATP and exposure onto X-ray film (See Example 3).

In another embodiment of the present invention, the oxidizing ion of a transition metal can be any transition metal ion, if it induces an oxidation of the TRAP protein. Preferably, the oxidizing ion of a transition metal can be selected among iron ($Fe^{2+}$), copper ($Cu^{2+}$) and zinc ($Zn^{2+}$). As described in Example 3, it is first identified that the TRAP protein is in vitro phosphorylated by using $FeSO_4$, $ZnCl_2$ or $CUCl_2$, while it is not phosphorylated using $Mg^{2+}$ commonly known to be required for a kinase activity (See FIG. 2).

$Mg^{2+}$ ion has been utilized for most of in vitro phosphorylations because it is a common ion for in vivo phosphorylation using a kinase ($Mg^{2+}$ ion exists a lot in intracellular mitochondria and the like) [Molecular Cell Biology, 5th Ed, page 77, FIG. 3-18]. However, the TRAP protein is first identified to be in vitro phosphorylated specifically by using transition metal ions such as iron ($Fe^{2+}$), copper ($Cu^{2+}$) or zinc ($Zn^{2+}$), and not by the $Mg^{2+}$ ion. Also, the phosphorylation is elucidated to be inhibited by a reducing agent such as ascorbic acid and thiolurea. Therefore, it is clarified that the TRAP has a feature to be oxidation-dependent in contrast to general kinases.

In accordance with another aspect of the present invention, there is provided a method for screening an inhibitor of the TRAP phosphorylation, which comprises steps: (a) in vitro mixing the TRAP protein, a phosphorylation buffer, oxidizing ions of a transition metal and ATP with a target substance; (b) measuring a degree of the TRAP phosphorylation by performing an in vitro kinase assay; and (c) judging the target substance as inhibitor of the TRAP phosphorylation if the TRAP phosphorylation decreases as compared to a control group.

In accordance with another embodiment of the present invention, the target substance can be any material for therapeutic use or natural substance separated from various animals and includes any inhibitory substance against the TRAP phosphorylation. Preferably, the control group can be the mixture of TRAP protein, a phosphorylation buffer, oxidizing ions of a transition metal and ATP excluding the target substance or including a substance having no inhibitory activity.

In another embodiment of the present invention, the in vitro kinase assay is to measure a degree of luminescence using a luciferase according to ATP consumption by a kinase. In the following Example 7, a high throughput screening for inhibitors against TRAP phosphorylation by using a Kinase Glo assay kit (purchased from Promega) is disclosed.

In accordance with another aspect of the present invention, there is provided a method for screening an inhibitor of the TRAP phosphorylation, which comprises steps: (a) in vitro mixing the TRAP protein, a phosphorylation buffer, oxidizing ions of a transition metal and $P^{32}$-ATP with a target substance; (b) measuring a degree of the TRAP phosphorylation by performing an SDS-PAGE of the mixture and then by exposing onto an X-ray film; and (c) judging the target substance as inhibitor of the TRAP phosphorylation if the TRAP phosphorylation decreases as compared to a control group.

In the following Example 6, the method for screening an inhibitor of the TRAP phosphorylation is disclosed. The TRAP is reacted with $P^{32}$-ATP, analyzed by performing a SDS-PAGE, gel-dried and exposed onto an X-ray film.

In accordance with another aspect of the present invention, there is provided a composition for the in vitro phosphorylation of TRAP, which comprises a TRAP protein, a phosphorylation buffer, oxidizing ions of a transition metal and ATP.

In the other embodiment of the present invention, the oxidizing ions of a transition metal can be any transition metal ion, if it induces an oxidation of the TRAP protein. Preferably, the oxidizing ion of a transition metal can be selected among iron ($Fe^{2+}$), copper ($Cu^{2+}$) and zinc ($Zn^{2+}$).

In the in vitro phosphorylation of the present invention, the TRAP protein can be phosphorylated in a short period by using metal ions as a subsidiary factor. Furthermore by using the procedure, inhibitors against the TRAP phosphorylation can be screened rapidly. Because the TRAP is an essential protein to infect *Staphylococcus aureus* in human, the inhibitors against TRAP phosphorylation are expected to develop novel antibiotics of *Staphylococcus aureus*, if selected by using the method of the present invention.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Practical and presently preferred embodiments of the present invention are illustrated as shown in the following examples. However, it will be appreciated that those skilled in the art may, on consideration of this disclosure, make modifications and improvements within the spirit and scope of the present invention.

Example 1

Cell Culture for Purification of TRAP Protein

Figure 1:
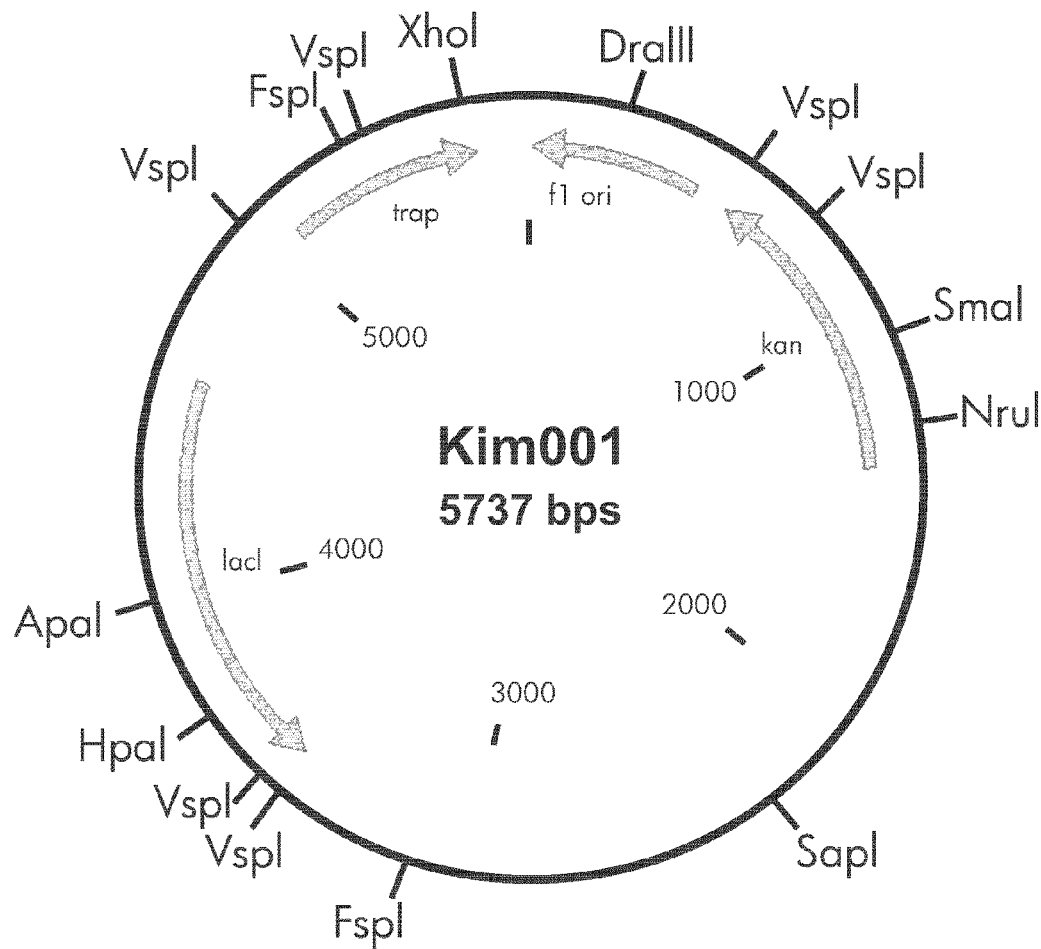
FIG. 1 is the restriction map of the TRAP expression vector (Kim001) of the present invention.

TRAP gene (SEQ ID NO:1, NCBI accession number: NC002952) was cloned into NcoI and XhoI sites of pet28a vector (purchased from Invitrogen). The expression vector Kim001 that can induce to produce an exogenous protein by IPTG and to express the TRAP protein having 6-histidine residues at the C-terminus was constructed (See FIG. 1). *Escherichia coli* transformant transformed with the expression vector Kim001 was cultured with culture broth for a bacterial expression. The compositions of culture broth are illustrated as follows.

TABLE 1

| Compositions of culture broth in *Escherichia coli* | |
|---|---|
| Ingredients | In 1 L |
| Peptone | 10 g |
| Yeast extract | 5 g |
| NaCl | 10 g |
| Kanamycin | 50 mg |

500 mL of the culture broth was poured into 1 L culture flask and sterilized under 15 atm of pressure at 121° C. for 15 minutes. Then, the *E. coli* transformant containing the expression vector Kim001 was inoculated into 5 mL of the culture broth, after pre-cultured with an LB/kan culture and cultured with stirring at 200 rpm for 24 hours. 5 mL of the resulting broth was re-inoculated into fresh broth and cultured at 37° C. with stirring at 200 rpm until reaching 0.3 to 0.6 of optical density (OD). Then, 1 mM IPTG was added and cultured again at 30° C. for 6 hours. The resulting cells were centrifuged at 6,000 rpm for 10 minutes, recovered and sonicated under ultrasonic power by adding a lysis buffer (50 mM Tris-HCl [pH8.0], 40 mM imidazole). The sonicated cells were centrifuged at 20,000 rpm for an hour to collect a cell supernatant used in the following Example 2.

Example 2

Purification of TRAP Protein

The cell supernatant obtained in the Example 1 was loaded onto a Hi trap chelating column (Amersharm Pharmacia) and recovered by using a collection buffer (50 mM Tris-HCL [pH 8.0], 0.5 to 1M imidazole). The resulting proteins were dialyzed to exchange the buffer with 0.5×PBS buffer. The protein sample was stored at 4° C. for an hour after adding 10 mM DTT. Finally, the protein sample was separated with HiLoad XK16/60 Superdex 75 gel-filtration column (Amersham-Pharmacia Biotech) by using 20 mM HEPES (pH 7.0) so as to purify the TRAP protein.

Example 3

Phosphorylation of TRAP Protein

The TRAP protein obtained in Example 2 was prepared with each tube according to following compositions of Table 2.

TABLE 2

| Compositions for phosphorylation | | | | | | | |
|---|---|---|---|---|---|---|---|
| | Lanes | | | | | | |
| | 1 | 2 | 3 | 4 | 5 | 6 | 7 |
| 10X phosphate buffer* | 1 μL | 1 μL | 1 μL | 1 μL | 1 μL | 1 μL | 1 μL |
| TRAP protein (50 μM) | 1 μL | 1 μL | 1 μL | 1 μL | 1 μL | 1 μL | 1 μL |
| Metal ions** (200, 2000 μM) | 1 μL | 1 μL | 1 μL | 1 μL | 1 μL | 1 μL | 1 μL |
| $P^{32}$-ATP (10 μCi) | 1 μL | 1 μL | 1 μL | 1 μL | 1 μL | 1 μL | 1 μL |
| DW | 6 μL | 6 μL | 6 μL | 6 μL | 6 μL | 6 μL | 6 μL |

Figure 2:
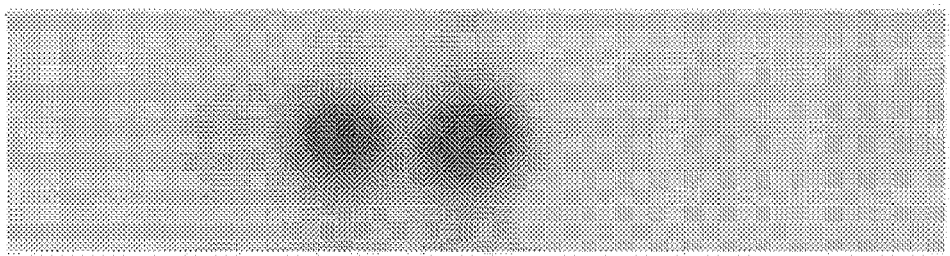
FIG. 2 is the treatment of various kinds of metal ions in order to identify conditions phosphorylating the TRAP.
Figure 2:
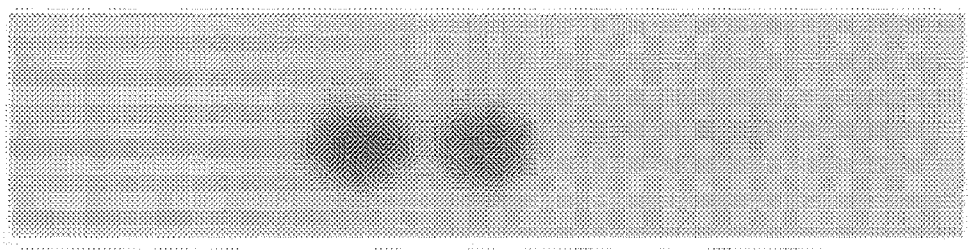

*Phosphate buffer: 20 mM HEPES [pH 7.0], 2.5% glycerol
**Metal ions: $MgCl_2$, $ZnCl_2$, $CuCl_2$, $CoCl_2$, $NiCl_2$, $CaCl_2$, $FeSO_4$ The protein sample prepared above was reacted at 37° C. for 30 minutes, then mixed with 2× loading dye 101 (BioRad), and analyzed by performing SDS-PAGE at 150 V for an hour. Afterward, the resulting gel was dried and exposed onto an X-ray film to measure a degree of phosphorylation. The result is illustrated in FIG. 2. In the upper part of FIG. 2, 20 μM metal ions, Mg, Zn, Cu, Fe, Mn, Ni, Co are used in Lane 1 through Lane 7, respectively. In the lower part of FIG. 2, 200 μM metal ions, Mg, Cu, Zn, Ni, Co, Ca are used in Lane 1 through Lane 7, respectively. As described in FIG. 2, it is identified that the TRAP protein is in vitro phosphorylated by using transition metal ions such as $FeSO_4$, $ZnCl_2$ and $CuCl_2$, while it was not phosphorylated by using $Mg^{2+}$ ions commonly known to be required for a kinase activity.

Example 4

TRAP Phosphorylation Dependent Upon Oxidative Reaction

Figure 5A:
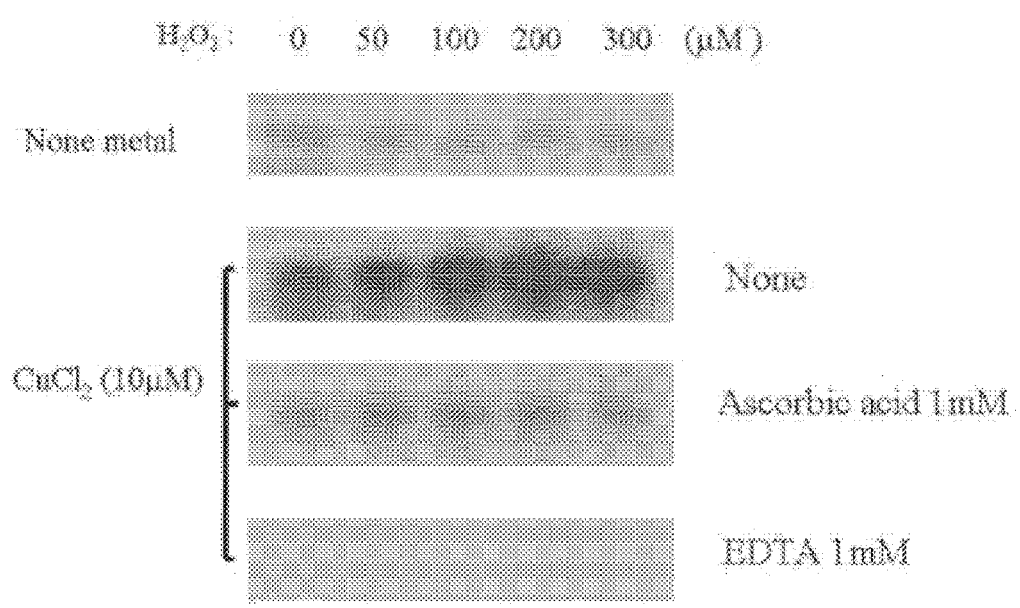
FIG. 5 is the experimental data of the present invention elucidating that the TRAP is phosphorylated by an oxidative reaction.
Figure 5B:
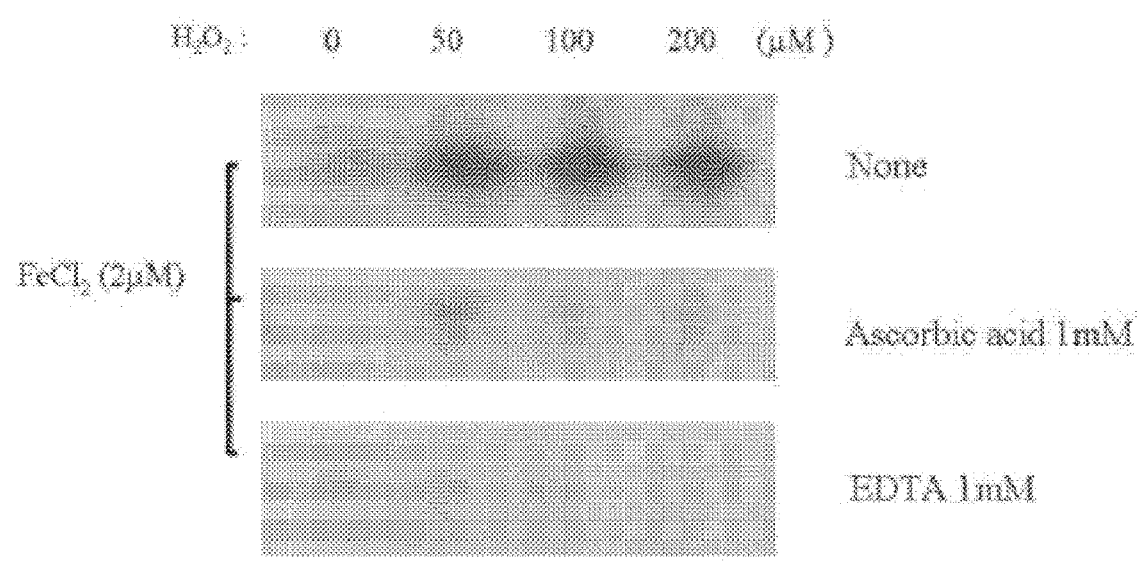

In order to prove that the TRAP phosphorylation is induced by an oxidative reaction, the present Example 4 is conducted as follows. Generally, a protein kinase binds with ATP, hydrolyzes ATP into ADP and attaches a resulting phosphate onto a specific amino acid of the protein to phosphorylate. In this process, $Mg^{2+}$ ions play a role of a subsidiary enzyme to stabilize the kinase binding with phosphates of ATP. However, the TRAP protein is phosphorylated by using transition metal ions such as $Fe^{2+}$, $Zn^{2+}$ and $Cu^{2+}$ without using $Mg^{2+}$ ions. The present inventors have attempted to elucidate why the TRAP protein utilizes the transition metal ions. Above all, we have suggested that the TRAP phosphorylation may be induced by an oxidative reaction of transition metal ions, because transition metals mediate an oxidative and reductive reaction of substance. Various oxidative and reductive agents were used to induce a phosphorylation in this Example. In order to identify a result of the phosphorylation, the same procedure of Example 3 is conducted. As a consequence, it is observed that the phosphorylation is induced by $H_2O_2$, a strong oxidative agent, and not by ascorbic acid (see FIG. 5). Therefore, it is confirmed that the TRAP phosphorylation should depend upon the oxidative reaction specifically.

Example 5

Quantitative Analysis of TRAP Phosphorylation

Figure 3:
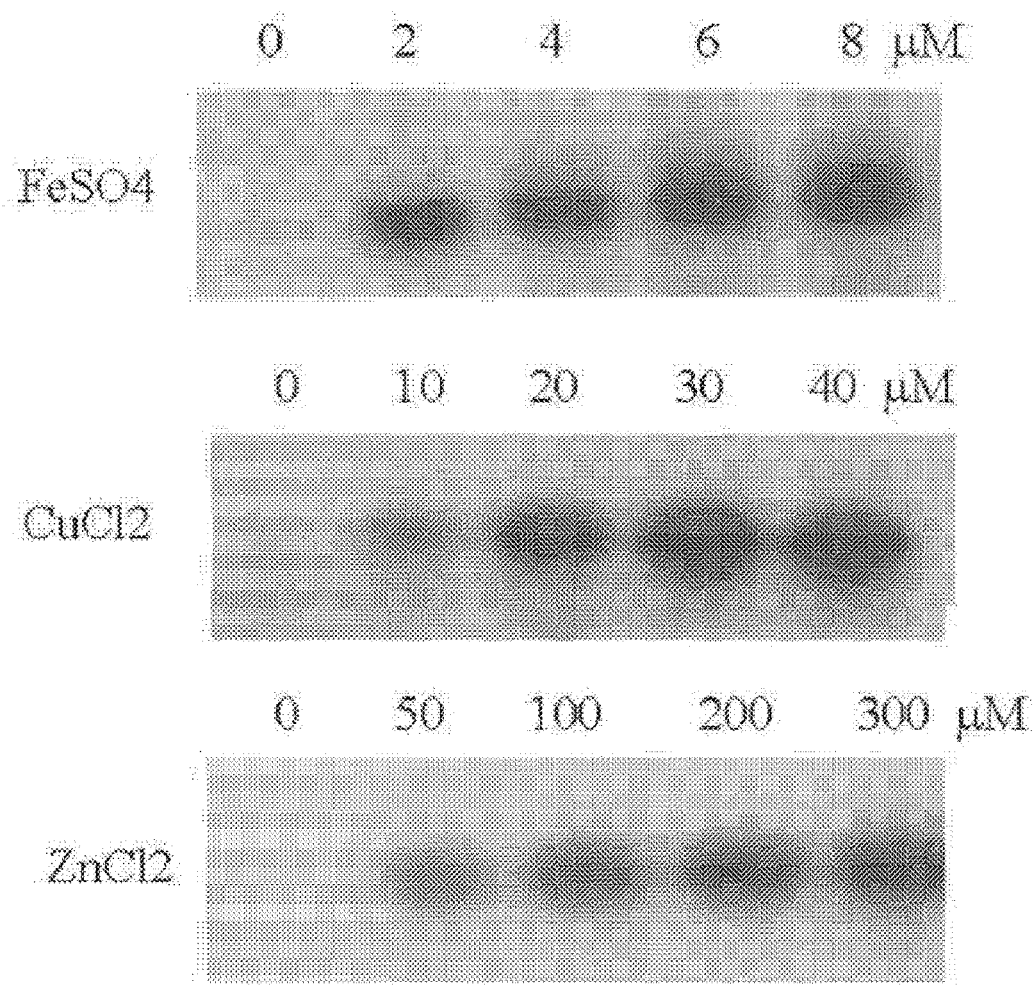
FIG. 3 is the quantitative data of metal ions phosphorylating the TRAP at each concentration.

In order to measure the TRAP phosphorylation, a quantitative analysis was performed by using $FeSO_4$, $ZnCl_2$ and $CuCl_2$, in this Example. $FeSO_4$, $ZnCl_2$ and $CuCl_2$, were added to each reaction at various ion concentrations and other conditions of the phosphorylation are the same as that of Example 3. The result is illustrated in FIG. 3. As described in FIG. 3, it is clarified that the TRAP protein is maximally phosphorylated above the concentrations of $FeSO_4$ (>2 μM), $CuCl_2$ (>20 μM) and $ZnCl_2$ (>100 μM).

Example 6

Screening of TRAP Inhibitor by Using TRAP Phosphorylation

A method for screening TRAP inhibitors by using the phosphorylation was developed in this Example. For this purpose, Prestwick Chemical Library (www.prestwick-chemical.fr/) was utilized. The compositions used for the phosphorylation is shown in following Table 3.

TABLE 3

| | Compositions used for phosphorylation | | | | | | |
|---|---|---|---|---|---|---|---|
| | Lanes | | | | | | |
| | 1 | 2 | 3 | 4 | 5 | 6 | 7 |
| 10X phosphate buffer | 1 μL | 1 μL | 1 μL | 1 μL | 1 μL | 1 μL | 1 μL |
| TRAP protein (50 μM) | 1 μL | 1 μL | 1 μL | 1 μL | 1 μL | 1 μL | 1 μL |
| $ZnCl_2$ or $CuCl_2$ (2 mM) | 1 μL | 1 μL | 1 μL | 1 μL | 1 μL | 1 μL | 1 μL |
| $P^{32}$-ATP (10 μCi) | 1 μL | 1 μL | 1 μL | 1 μL | 1 μL | 1 μL | 1 μL |
| Prestwick Library | 1 μL | 1 μL | 1 μL | 1 μL | 1 μL | 1 μL | 1 μL |
| DW | 5 μL | 5 μL | 5 μL | 5 μL | 5 μL | 5 μL | 5 μL |
| Total | 10 μL | 10 μL | 10 μL | 10 μL | 10 μL | 10 μL | 10 μL |

Figure 4:
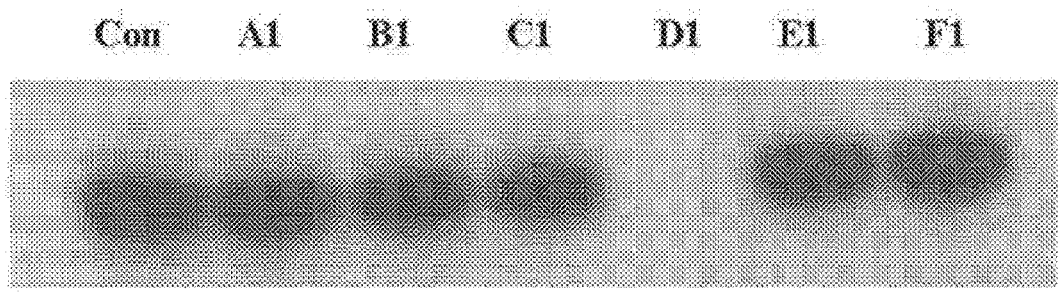
FIG. 4 is the screening data of TRAP inhibitors by using the method for screening an inhibitor of the TRAP phosphorylation.

In order to identify a result of the phosphorylation, the same procedure of the Example 3 is conducted. In addition to the above-mentioned compositions and methods, various substances can be examined with other tubes. The result is illustrated in FIG. 4. In FIG. 4, lane 1 is Con (negative control) and Lane 2 through Lane 7 are chemicals A1, B1, C1, D1, E1 and F1 of Prestwick Library, respectively. As demonstrated above, the TRAP phosphorylation is verified to be inhibited by chemical D1. As a consequence, it is identified that this procedure can be used to screen inhibitors against the TRAP phosphorylation rapidly.

Example 7

Screening of TRAP Inhibitor by Using High Throughput Screening (HTS)

Figure 6A:
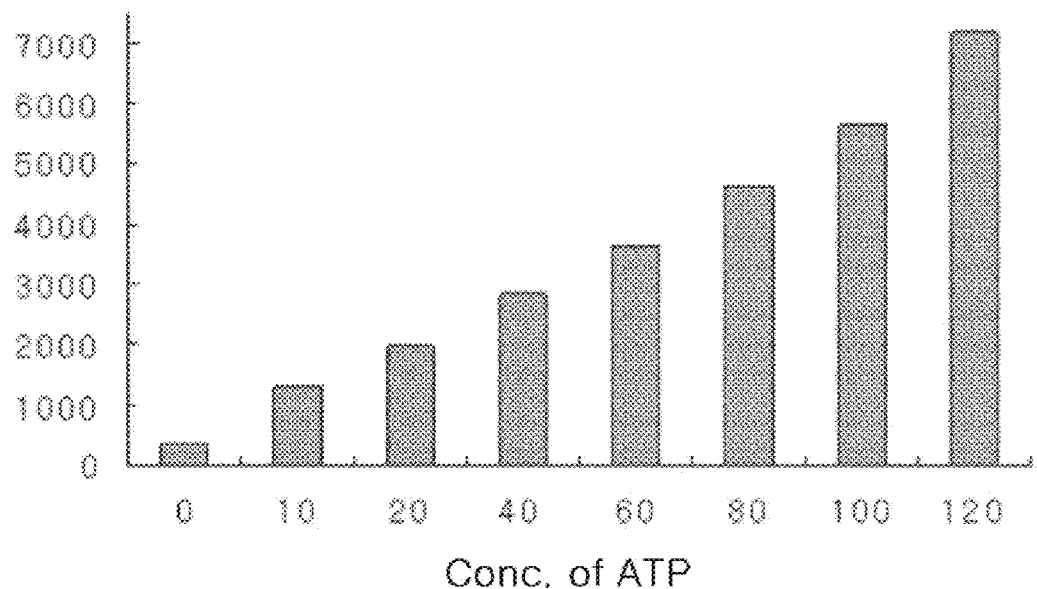
FIG. 6 is the experimental data measured by the method for screening an inhibitor of the TRAP phosphorylation using a high throughput screening.
Figure 6B:
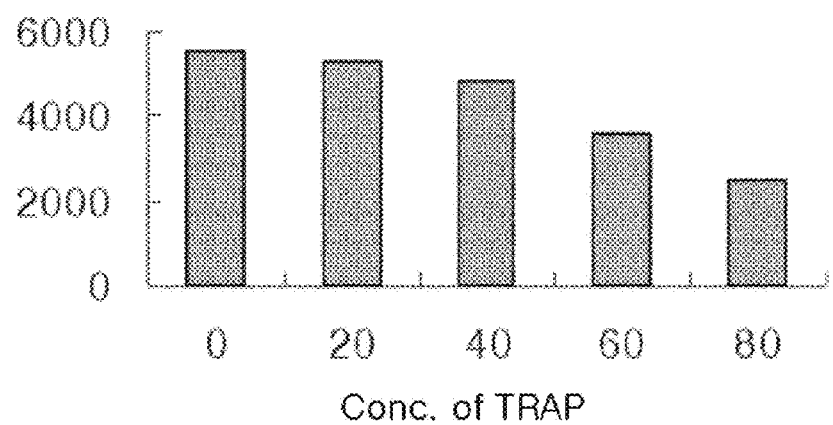
Figure 6C:

Kinase transfers γ-phosphate of ATP toward a substrate or its phosphorylation site by a catalysis. Based upon this principle, the amount of ATP consumption can be measured to monitor a kinase activity. In this Example, a high throughput screening for TRAP inhibitors by using a Kinase Glo assay kit (purchased from Promega) is suggested. The Kinase Glo assay kit is to measure a degree of luminescence using a luciferase according to ATP consumption by a kinase. In detail, Kinase Glo buffer and a substrate were reacted at room temperature for 30 minutes. 50 µM TRAP protein was allotted to a 9×6 well plate in 91 µL and then, candidate chemicals of inhibitors were added in 1 µL (500 µM) respectively. 10 µL of ATP (100 µM) was added and reacted at 37° C. for 30 minutes. 20 µL of Glo mixture was added and reacted at room temperature for 20 minutes to measure a degree of luminescence at 560 nm. FIG. 6a is a graph that measures a luciferase activity according to ATP concentrations (µM) in order to identify whether the Kinase assay kit operates successfully. The luciferase activity is observed to increase in accordance with the ATP concentration. FIG. 6b is a graph that measures a luciferase activity according to TRAP concentrations (µM). The luciferase activity is observed to decrease in accordance with TRAP concentrations, because the TRAP degrades ATPs. The kinase activity elevated as the luciferase activity decreased. FIG. 6c is a graph that measures a luciferase activity when thiolurea is used for a phosphorylation inhibitor. In order to screen inhibitors against TRAP phosphorylation, 100 µM of ATP and 100 µM of TRAP were used with a 9×6 well plate and thiolurea (2 mM) was added as a strong reducing agent. Lane 1 is a luciferase activity without TRAP; lane 2, a luciferase activity with TRAP; and lane 3 is a luciferase activity by adding thiolurea. As a consequence, the strong reducing agent is identified to obstruct the phosphorylation by inhibiting a TRAP oxidation. Based upon this result, it is also confirmed that another kinds of inhibitors can be screened by the same procedure with the above.

While the present invention has been particularly shown and described with reference to exemplary embodiments thereof, it will be understood by those skilled in the art that various changes in form and details may be made therein without departing from the spirit and scope of the present invention as defined by the appended claims.

What is claimed is:

1. A method for in vitro phosphorylation of TRAP (target of RNA III-activating protein) comprising in vitro mixing and incubating a phosphorylation buffer, oxidizing ions of a transition metal and ATP (Adenosine Tri-Phosphate), with TRAP purified from cells, and detecting phosphorylation of TRAP.

2. The method for in vitro phosphorylation of TRAP as set forth in claim 1, wherein the TRAP is separated and purified from an *Escherichia coli* transformant transformed with a TRAP expression vector after being expressed in a large scale.

3. The method for in vitro phosphorylation of TRAP as set forth in claim 1, further comprising measuring a degree of phosphorylation of TRAP after the mixing and incubation step.

4. The method for in vitro phosphorylation of TRAP as set forth in claim 1, wherein the oxidizing ion of a transition metal is selected from the group consisting of iron ($Fe^{2+}$), copper ($Cu^{2+}$) and zinc ($Zn^{2+}$).

5. A method for screening an inhibitor of TRAP phosphorylation comprising: (a) in vitro mixing TRAP protein, a phosphorylation buffer, oxidizing ions of a transition metal and ATP with a target substance; (b) measuring a degree of TRAP phosphorylation by performing an in vitro kinase assay; and (c) determining the target substance as inhibitor of TRAP phosphorylation if the TRAP phosphorylation decreases as compared to a control group.

6. The method for screening an inhibitor of TRAP phosphorylation as set forth in claim 5, wherein the in vitro kinase assay comprises measuring a degree of luminescence using a luciferase according to ATP consumption by a kinase.

7. A method for screening an inhibitor of TRAP phosphorylation comprising: (a) in vitro mixing TRAP protein, a phosphorylation buffer, oxidizing ions of a transition metal and ATP with a target substance; (b) measuring a degree of TRAP phosphorylation by performing SDS-PAGE of the mixture and then by exposing onto an X-ray film; and (c) determining the target substance as inhibitor of TRAP phosphorylation if the TRAP phosphorylation decreases as compared to a control group.

8. A composition consisting of a TRAP protein, a phosphorylation buffer, oxidizing ions of a transition metal and ATP.

9. The composition as set forth in claim 8, wherein the oxidizing ion of a transition metal is selected from the group consisting of iron ($Fe^{2+}$), copper ($Cu^{2+}$) and zinc ($Zn^{2+}$).

* * * * *